(12) United States Patent
Varona et al.

(10) Patent No.: US 10,307,298 B2
(45) Date of Patent: Jun. 4, 2019

(54) MULTI-LAYERED ABSORBENT ARTICLE

(71) Applicant: DSG TECHNOLOGY HOLDINGS LTD, Kwai Chung (HK)

(72) Inventors: Gene Varona, Marietta, GA (US); Patrick King Yu Tsang, Derbyshire (GB); Andrew Wright, Derbyshire (GB)

(73) Assignee: DSG Technology Holdings Ltd., Kwai Chung, N.T. (HK)

( * ) Notice: Subject to any disclaimer, the term of this patent is extended or adjusted under 35 U.S.C. 154(b) by 0 days.

(21) Appl. No.: 15/435,364

(22) Filed: Feb. 17, 2017

(65) Prior Publication Data

US 2017/0181898 A1      Jun. 29, 2017

Related U.S. Application Data

(63) Continuation of application No. 14/216,173, filed on Mar. 17, 2014, now Pat. No. 9,687,394.

(Continued)

(51) Int. Cl.
*A61F 13/15* (2006.01)
*A61F 13/539* (2006.01)
(Continued)

(52) U.S. Cl.
CPC .............................. *A61F 13/15658* (2013.01); *A61F 13/49011* (2013.01); *A61F 13/539* (2013.01);
(Continued)

(58) Field of Classification Search
CPC .... A61F 13/15658; A61F 2013/530131; A61F 2013/5349; A61F 2013/53975
(Continued)

(56) References Cited

U.S. PATENT DOCUMENTS 4,025,671 A    5/1977  Creamer
4,425,127 A    1/1984  Suzuki et al.
(Continued)

FOREIGN PATENT DOCUMENTS

CN         1134271 A       10/1996
CN      102844009 A       12/2012
(Continued)

OTHER PUBLICATIONS

Appeal Brief filed in U.S. Appl. No. 09/242,482, filed Oct. 22, 1999 (now issued as U.S. Pat. No. 8,268,424 dated Sep. 18, 2012), filed Dec. 19, 2011 [24 pages].

(Continued)

*Primary Examiner* — Jacqueline F Stephens
(74) *Attorney, Agent, or Firm* — Alberto Q. Amatong, Jr.; Amatong McCoy LLC

(57) ABSTRACT

A thin absorbent composite is provided wherein a nonwoven support sheet is hydro-entangled with a carded fiber web to provide a nonwoven substrate. The nonwoven substrate is coated with an absorbent layer comprising microfibrillated cellulose-coated superabsorbent polymer particles. A cover layer is placed above the absorbent layer to provide the absorbent composite. A process for manufacturing the absorbent composite and an absorbent article containing the absorbent composite are also provided.

31 Claims, 17 Drawing Sheets

Related U.S. Application Data

(60) Provisional application No. 61/799,075, filed on Mar. 15, 2013.

(51) Int. Cl.
*A61F 13/49* (2006.01)
*A61F 13/58* (2006.01)
*A61L 15/22* (2006.01)
*A61L 15/42* (2006.01)
*A61F 13/53* (2006.01)
*A61F 13/534* (2006.01)

(52) U.S. Cl.
CPC ............ *A61F 13/58* (2013.01); *A61L 15/225* (2013.01); *A61L 15/42* (2013.01); *A61F 2013/5349* (2013.01); *A61F 2013/530131* (2013.01); *A61F 2013/530343* (2013.01); *A61F 2013/530591* (2013.01); *A61F 2013/53975* (2013.01)

(58) Field of Classification Search
USPC .................................. 604/372, 367, 370, 374
See application file for complete search history.

(56) References Cited

U.S. PATENT DOCUMENTS

| | | | |
|---|---|---|---|
| 4,762,521 A | 8/1988 | Roessler et al. | |
| 4,773,903 A | 9/1988 | Weisman et al. | |
| 4,784,892 A | 11/1988 | Storey et al. | |
| 4,911,700 A | 3/1990 | Makoui et al. | |
| 5,047,456 A | 9/1991 | Onwumere et al. | |
| 5,387,208 A | 2/1995 | Ashton et al. | |
| 5,436,066 A | 7/1995 | Chen | |
| 5,651,862 A | 7/1997 | Anderson et al. | |
| 5,763,044 A | 6/1998 | Ahr et al. | |
| 5,821,179 A | 10/1998 | Masaki et al. | |
| 6,068,620 A | 5/2000 | Chmielewski | |
| 6,086,950 A | 7/2000 | Masaki et al. | |
| 6,368,990 B1 | 4/2002 | Jennergren et al. | |
| 6,540,853 B1 | 4/2003 | Suzuki et al. | |
| 6,790,798 B1 * | 9/2004 | Suzuki | A61F 13/15658 442/373 |
| 6,794,557 B1 | 9/2004 | Klemp et al. | |
| 6,972,011 B2 | 12/2005 | Maeda et al. | |
| 7,087,044 B2 | 8/2006 | Ohnishi | |
| 7,101,438 B2 | 9/2006 | Suzuki et al. | |
| 8,268,424 B1 | 9/2012 | Suzuki et al. | |
| 2001/0014797 A1 | 8/2001 | Suzuki et al. | |
| 2004/0015142 A1 | 1/2004 | Johnston et al. | |
| 2004/0127869 A1 * | 7/2004 | Hu | D21C 9/001 604/376 |
| 2004/0211361 A1 | 10/2004 | Suzuki et al. | |
| 2005/0143703 A1 | 6/2005 | Persson | |
| 2005/0165371 A1 | 7/2005 | Giacometti | |
| 2009/0062760 A1 | 3/2009 | Wright et al. | |
| 2010/0062165 A1 | 3/2010 | Suzuki et al. | |
| 2010/0062934 A1 | 3/2010 | Suzuki et al. | |
| 2010/0063470 A1 | 3/2010 | Suzuki et al. | |
| 2011/0130736 A1 | 6/2011 | Tsang et al. | |
| 2012/0053547 A1 | 3/2012 | Schroeder et al. | |

FOREIGN PATENT DOCUMENTS

| | | |
|---|---|---|
| DE | 4341443 C1 | 3/1995 |
| EP | 0209884 A2 | 1/1987 |
| EP | 0210570 A1 | 2/1987 |
| EP | 0513390 A1 | 11/1992 |
| EP | 0719531 A1 | 7/1996 |
| EP | 0947549 A1 | 10/1999 |
| EP | 1116479 A2 | 7/2001 |
| JP | H10168230 A | 6/1998 |
| JP | 2010119743 A | 6/2010 |
| JP | 2013039804 A | 2/2013 |
| WO | 9702946 A1 | 1/1997 |
| WO | 2005060892 A1 | 7/2005 |
| WO | 2011128790 A2 | 10/2011 |

OTHER PUBLICATIONS

Final Office Action issued in U.S. Appl. No. 09/242,482, filed Oct. 22, 1999 (now issued as U.S. Pat. No. 8,268,424 dated Sep. 18, 2012), dated Feb. 16, 2011 [7 pages].

International Preliminary Report on Patentability issued in PCT Application No. PCT/US2014/030066, dated Sep. 24, 2015; 12 pages.

International Search Report and Written Opinion issued in PCT Application No. PCT/US2014/030066, dated Aug. 27, 2014; 13 pages.

Supplementary EP Search Report, issued in EP Application No. 14764643.4 dated Sep. 28, 2016 [11 pages].

* cited by examiner

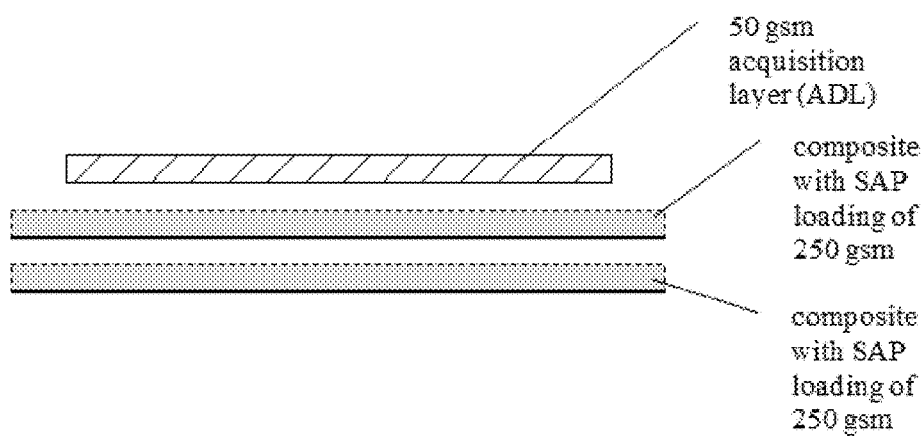
Figure 11A: Core A – cross-section view
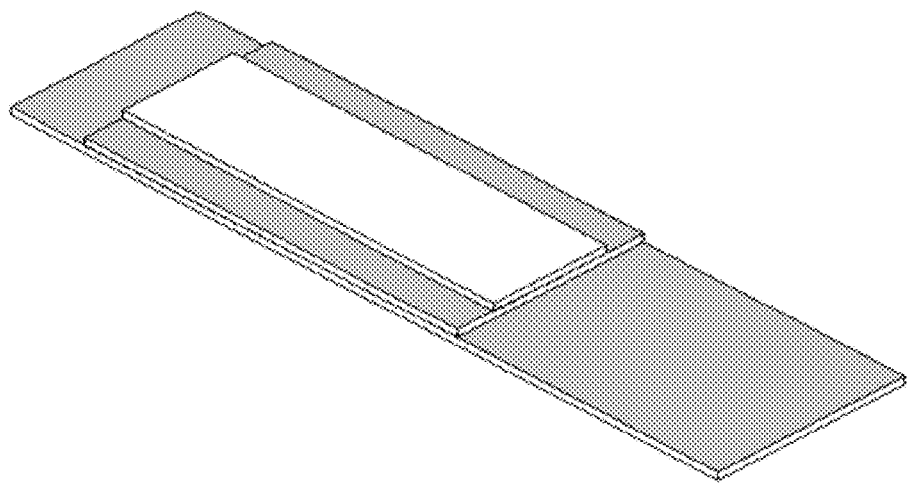
Figure 11B: Core A – perspective view

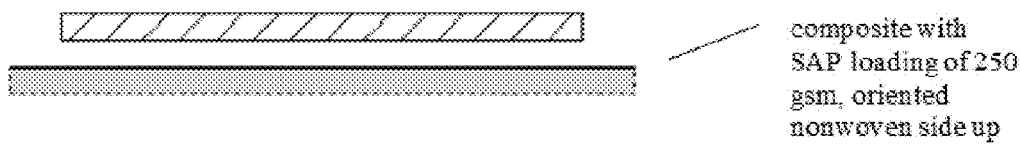
Figure 12: Core B – cross-section view
Figure 13: Core C – cross-section view (high SAP loading, high basis weight carded fiber)

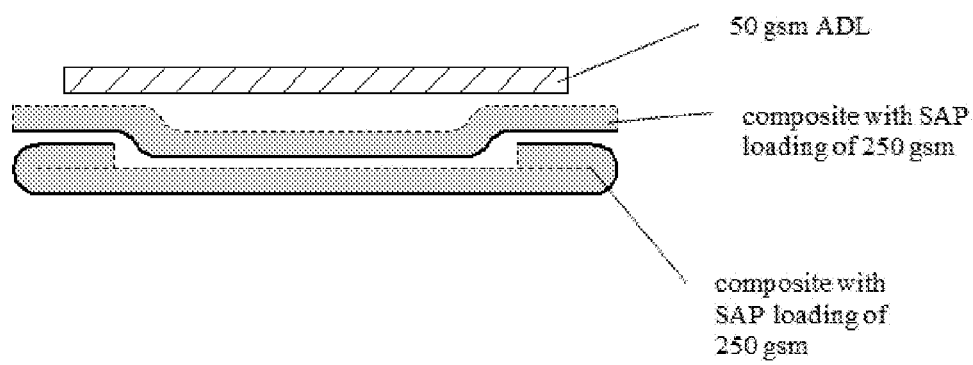
Figure 14A: Core D – cross-section view
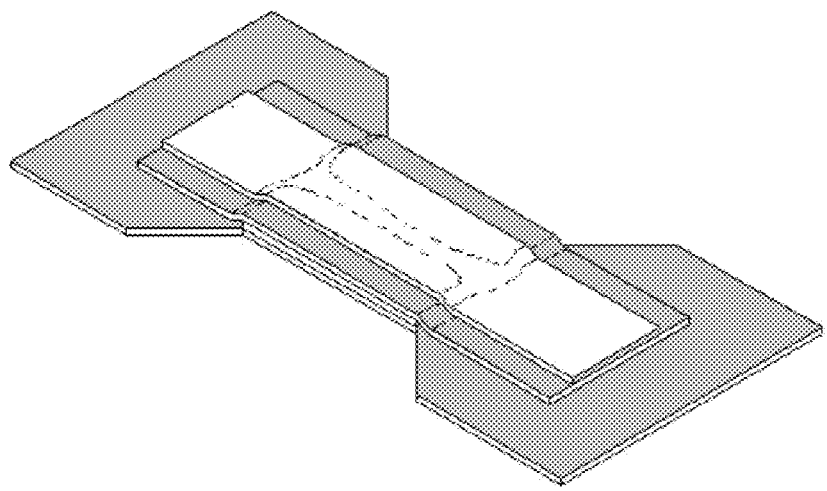
Figure 14B: Core D – perspective view

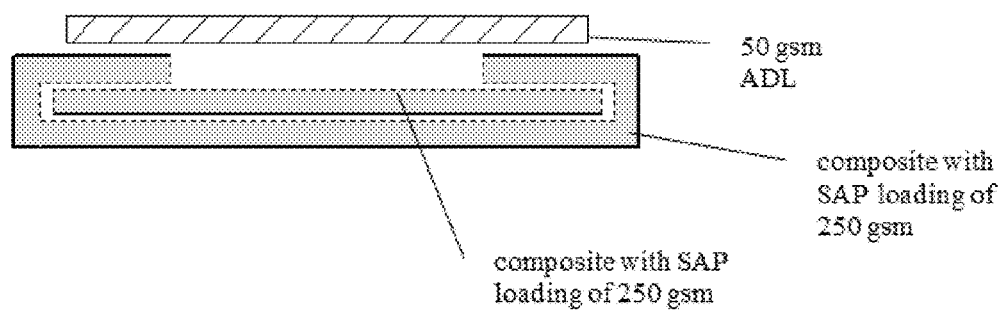
Figure 15A: Core E – cross-section view
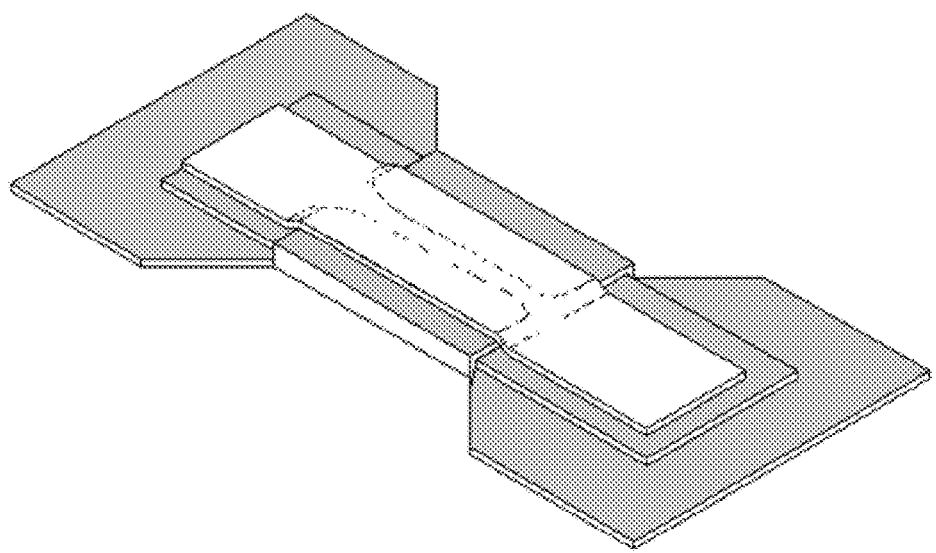
Figure 15B: Core E – perspective view

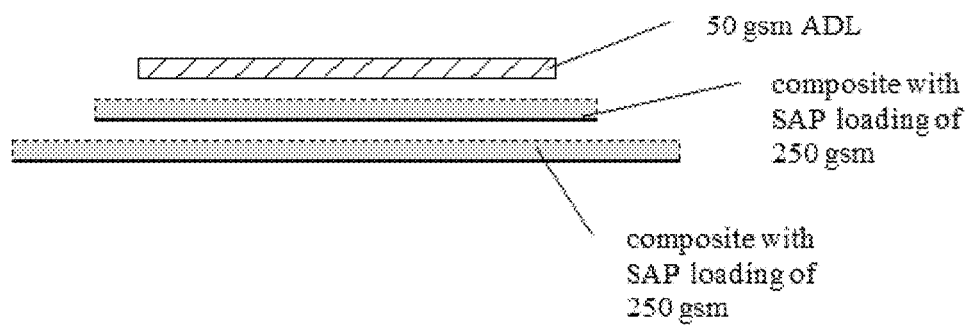
Figure 16A: Core F: cross-section view
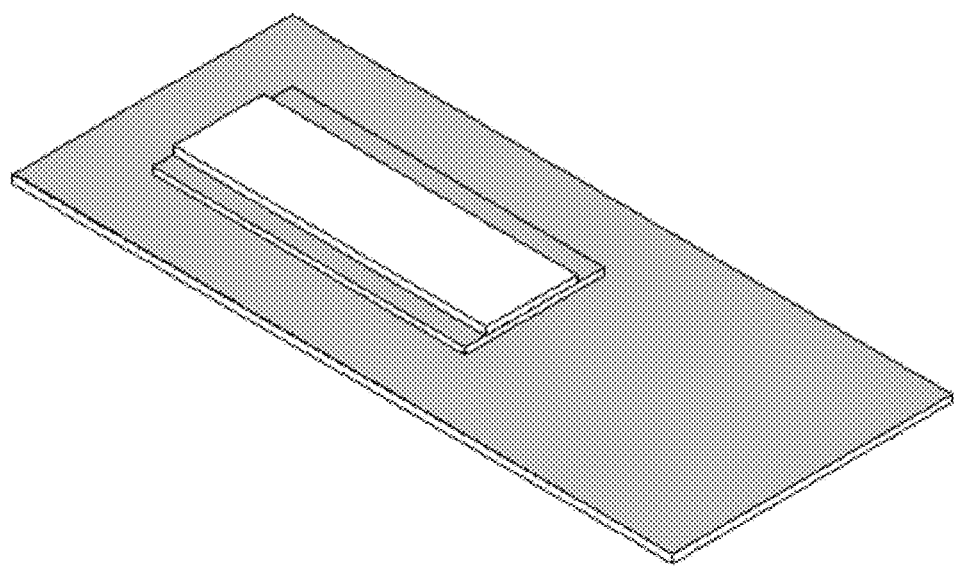
Figure 16B: Core F: perspective view

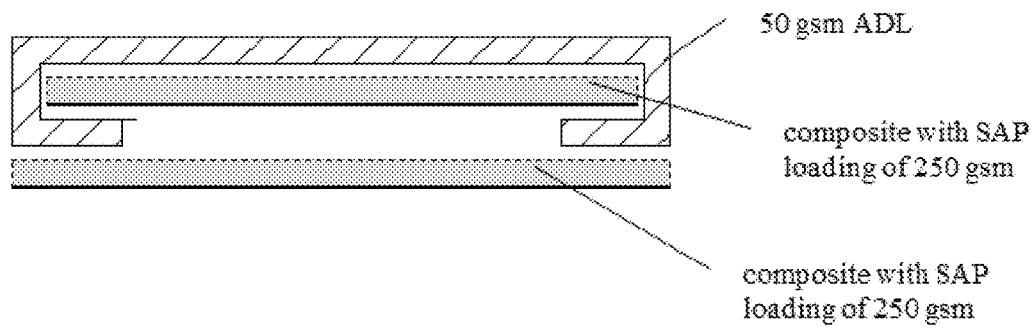
Figure 17A: Core G: cross-section view
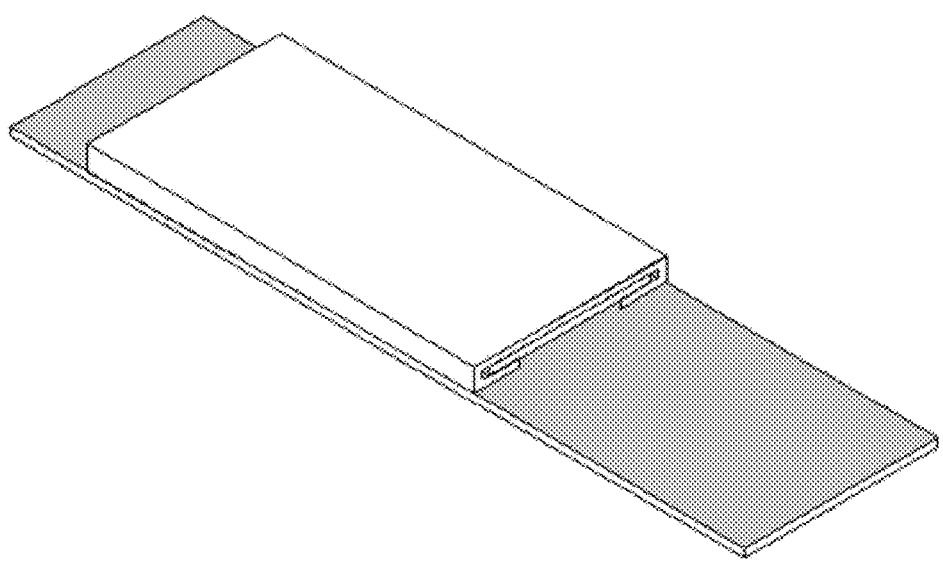
Figure 17B: Core-G: perspective view

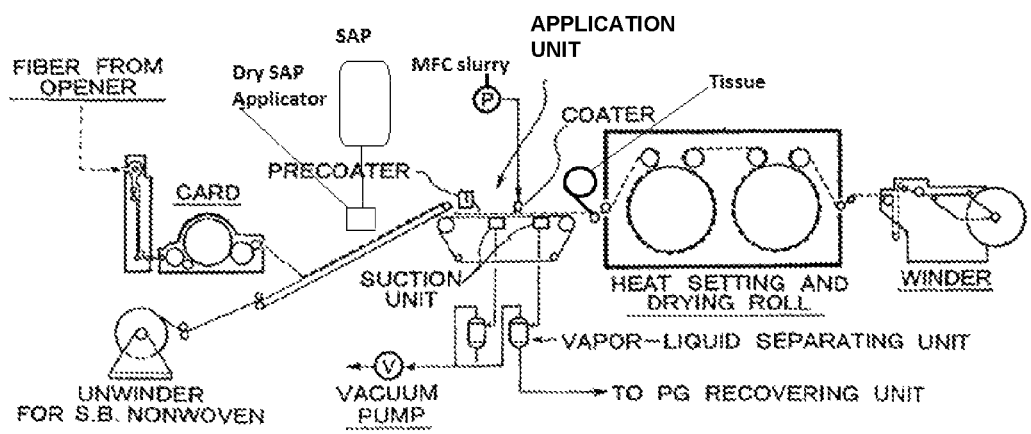
Figure 18: Hybrid composite production process
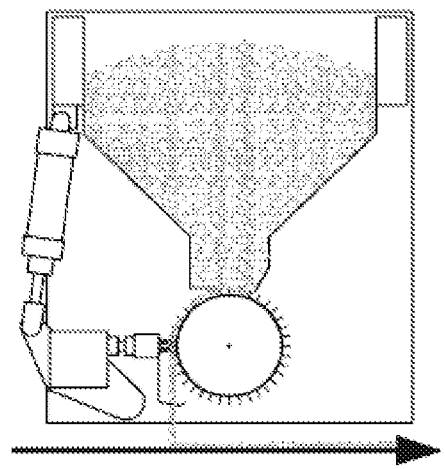
Figure 19: SAP scattering unit

MULTI-LAYERED ABSORBENT ARTICLE

The present application claims the benefit of U.S. Provisional Application Ser. No. 61/799,075, filed on Mar. 15, 2013, which disclosure is hereby incorporated by reference for all purposes and made a part of the present disclosure.

BACKGROUND OF THE INVENTION

The present invention relates to an absorbent composite, and in particular, an absorbent composite with an absorbent layer comprising micro-fibrillated cellulose-coated super absorbent polymer. The present invention also relates to a method of making the absorbent composite and to disposable absorbent articles employing absorbent composite. Disposable absorbent articles include diapers, youth pants, training pants, adult incontinence products, bodily exudates absorbing products, feminine hygiene products, and other absorbent products (collectively "disposable absorbent articles").

Prior disposable absorbent articles typically employ three basic structural elements: a topsheet that forms the inner surface, a backsheet that forms the outer surface, and an absorbent core that is interposed between the top sheet and the backsheet. The topsheet is designed to allow liquid to pass from outside the absorbent article through the topsheet and into the absorbent core. The topsheet may be made out of a range of liquid and vapor permeable hydrophilic or hydrophobic materials. The permeability of the topsheet can be increased by using surface activation agents ("surfactants"). Surfactants lower the surface energy or the contact angle of the liquid-solid interface and facilitate the liquid's passage through the top sheet.

The backsheet is designed to prevent fluid from passing from the absorbent core through the backsheet and out of the absorbent article. The backsheet may be made out of an impermeable film that extends the full width of the article or a combination of cloth-like material and impermeable film. The backsheet may also have vapor transmission properties ("breathability") that allow vapor to pass through the backsheet without releasing fluid stored in the absorbent core. The backsheet may also be made from a liquid impermeable but vapor transmittable non-woven material such as spunbond, melt-blow, spun-bond ("SMS"); spun-bond, melt-blown, melt-blown, spun-bond ("SMMS"); micro, nano, or splitable fibers; spun melt or spun laced; carded; and the like.

The absorbent core is designed to contain and distribute fluid that passes through the topsheet. A typical absorbent core is made out of a high or super absorbent polymer (SAP) stabilized by an absorbent matrix. SAP is commonly made out of materials such as polyvinyl alcohol, polyacrylates, various grafted starches, and cross-linked sodium polyacrylate. SAP can be in the form of particles, fibers, foams, web, spheres, agglomerates of regular or irregular shapes, and film. The absorbent matrix is typically a de-fiberized wood pulp or similar material. The absorbent matrix is very bulky relative to the topsheet, backsheet, and SAP. Traditionally, most of a diaper's thickness has come from the absorbent core.

Increasingly, consumers of absorbent articles are demanding thinner absorbent articles. To meet these demands, manufacturers are decreasing the thickness of absorbent articles by decreasing the amount of absorbent matrix used in absorbent cores. Although the resulting absorbent cores are thinner, they suffer in performance. As the amount of absorbent matrix is reduced, it is less effective in stabilizing the SAP-preventing the SAP from migrating within the absorbent core. As SAP migrates within the core, the absorbent core loses its effectiveness and no longer has uniform absorbency. For example, SAP that is not contained tends to collect in wetted areas and is inefficient for handling subsequent discharges.

Manufactures have attempted to solve this problem by creating small, individual SAP pockets or by gluing the SAP. These solutions, however, have been largely unsuccessful. The SAP pockets merely limit the migration to movement within the pockets. However, because there is still movement of the particles, the absorbent core does not exhibit uniform absorbency. Gluing stabilizes the SAP, but results in an uncomfortably stiff absorbent core and a loss in the SAP's swelling capacity.

Accordingly, there exists a need for an improved absorbent product that continues the trend of decreasing product thickness, while minimizing product stiffness and exhibiting excellent absorbency.

BRIEF SUMMARY OF THE INVENTION

The present invention includes an absorbent composite, a method for making the absorbent composite, and an absorbent article containing the absorbent composite. The absorbent composite comprises a nonwoven substrate, an absorbent layer, and a cover layer. The nonwoven substrate comprises a nonwoven support sheet, for example, a polypropylene spunbond (PPSB) nonwoven support sheet, attached to a carded fiber web through a hydro-entanglement process. The absorbent layer comprises microfibrillated cellulose-coated superabsorbent polymer. The manufacturing process for the absorbent composite comprises the following steps: (1) carding of fibers, for example, polyester (PET) fibers to form a carded web; (2) placing the carded web on top of the nonwoven supporting sheet; (3) mechanically joining the carded web with the nonwoven supporting sheet through hydro-entanglement to form a nonwoven substrate; (4) preparing an MFC-coated SAP slurry by combining, preferably homogenously, a mixture of SAP slurry (SAP in a solvent, preferably ethanol and water) with a mixture of MFC slurry (MFC in a solvent, preferably ethanol and water); (5) applying the MFC-coated SAP slurry to the nonwoven substrate; (6) withdrawing excess liquid from the nonwoven substrate with a vacuum force; (7) placing a cover layer on top of the MFC-coated SAP surface; (8) drying the composite with heat and suction units to facilitate the collection and recovery of solvent; (9) optionally treating the nonwoven substrate side of the composite with surfactant; (10) optionally, winding the absorbent composite web into a mother roll; and (11) optionally, dividing the mother roll into narrower rolls of composite material using a slitter. The present invention also includes an absorbent article comprising a liquid-permeable topsheet, a liquid-impermeable backsheet and an absorbent composite, which comprises a nonwoven substrate that includes carded fiber, preferably to provide high loft to the resulting carded nonwoven, SAP particles, and micro-fibrillated fibers for helping to immobilize the SAP within the carded nonwoven.

BRIEF DESCRIPTION OF THE DRAWINGS

FIG. 11A illustrates the absorbent core A embodiment, comprising two 250 gsm absorbent composites and an ADL. The ADL is positioned above two absorbent composite layers of equal width. The ADL is adjacent to the MFC-coated SAP side of the absorbent composite.

FIG. 11B is a perspective view of core A displaying different lengths of the absorbent composites. The ADL is narrower, but equal in length to the upper composite. The lower composite is longer, but equal in width to the upper composite.

FIG. 12 illustrates the core B embodiment, wherein the absorbent composite is oriented with the MFC-coated SAP side of the absorbent composite facing away from the body and the ADL adjacent to the nonwoven substrate face of the absorbent composite. The core B embodiment includes SAP loading of 250 gsm.

FIG. 13 is a cross-section of the core C embodiment with 350 gsm SAP loading and an 80 gsm carded fiber web.

FIG. 14A illustrates the core D embodiment that includes a dual absorbent composite configuration with the upper absorbent composite disposed above a folded lower absorbent composite.

FIG. 14B is a perspective view of the core D embodiment depicting the topography resulting from the stacked, folded composite configuration.

FIG. 15A depicts the core E embodiment that includes a first absorbent composite wrapped around the lateral edges of a second absorbent composite and an ADL disposed above the two composites.

FIG. 15B is a perspective view of the core E embodiment.

FIG. 16A depicts the core F embodiment that includes an ADL disposed above two absorbent composite layers of unequal width. The ADL is adjacent to the composite face which is predominantly composed of MFC-coated SAP.

FIG. 16B is a perspective view of the core F embodiment. The ADL is equal in length to the upper composite and shorter and narrower than the lower compsite.

FIG. 17A illustrates the core G embodiment, wherein an ADL is wrapped around the lateral edges of a first, upper absorbent composite. The ADL-wrapped first absorbent composite is disposed above a second, wider absorbent composite.

FIG. 17B is a perspective view of the core G embodiment. The folded ADL results in a configuration that is equal in width to the lower composite.

FIG. 18 is a schematic detailing the hybrid absorbent composite production process.

FIG. 19 is a SAP scattering unit that is used to disperse SAP onto the moving absorbent composite web in the hybrid production process.

DETAILED DESCRIPTION OF THE INVENTION

Figure 1A:
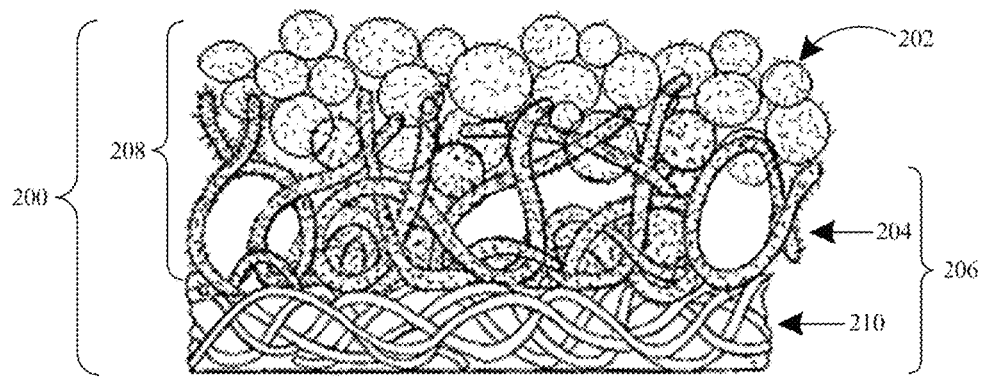
FIG. 1A depicts, in exaggerated fashion, the preferred absorbent composite structure. The composite includes the nonwoven support sheet 210, for example, a polypropylene spunbond nonwoven support sheet, the carded fiber web 204, and the absorbent layer comprising MFC-coated SAP 202. The MFC-coated SAP is situated as a uniform layer on the carded fiber web.

Upon review of the detailed description and the accompanying drawings provided herein, it will be apparent to one of ordinary skill in the art that an absorbent composite made according to the present invention may be used in disposable absorbent articles, and more particularly, in disposable absorbent articles, such as diapers, training pants or other incontinence products. Accordingly, the present invention shall not be limited to the structures and processes specifically described and illustrated herein, although the following description is particularly directed to an absorbent composite that is used in a disposable diaper. The term "absorbent article" or "absorbent garment" with which the present invention is associated, includes various types of disposable articles and garments which are placed against or in proximity to the body of the wearer so as to absorb and contain various bodily exudates, bodily fluid, or biofluid.

Absorbent Composite

FIG. 1 depicts (in exaggerated fashion for illustration) an absorbent composite 200 employed in various embodiments of the present invention. The absorbent composite 200 is a sheet comprising water-swellable bodies in the form of super absorbent polymer particles 202 (SAP) which are covered or intermixed with extremely fine micro-fibrillated cellulose (MFC) (not numbered). In particular, a layer of MFC-coated SAP is uniformly distributed onto and suspended in carded fibers or the carded web 204. The carded fibers 204 along with the suspended MFC-coated SAP form the carded-fiber layer 208 of the absorbent composite 200. In addition, the absorbent composite 200 also includes a nonwoven, preferably a polypropylene spun bond (PPSB), support sheet 210. The carded fibers 204 and the nonwoven support sheet 210 are joined to one another through hydro-entanglement and form the nonwoven substrate 206 of the absorbent composite 200.

It is possible to produce the absorbent composite such that the SAP is present in the composite in both a uniform and a non-uniform distribution. In the non-uniform construction, the SAP can be arranged in discrete lines, pockets or other configurations, separated by regions substantially devoid of SAP. However, the preferred embodiment of the absorbent composite includes uniformly distributed MFC-coated SAP, i.e. the SAP is evenly distributed over the surface of the carded web.

Figure 2:
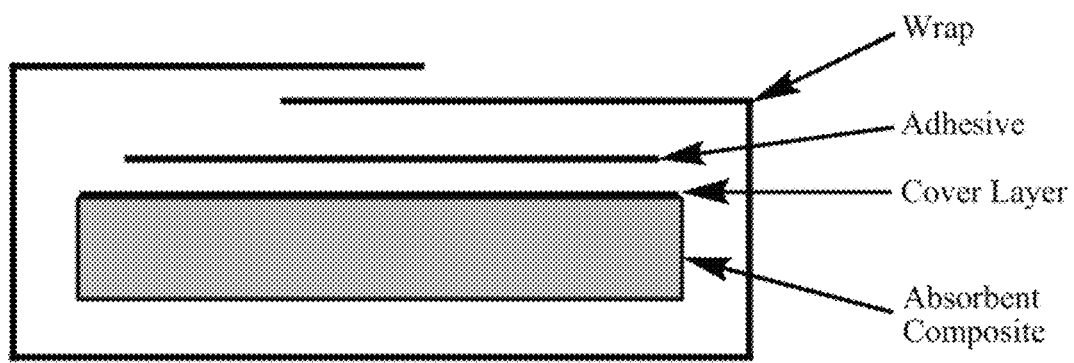
FIG. 2 depicts a wrapped configuration of the absorbent composite.

In addition, a cover layer is located above the absorbent layer. FIG. 2 depicts the absorbent composite with a cover layer. The cover layer may comprise tissue or a nonwoven fabric. The cover layer is substantially co-extensive with the MFC-coated SAP layer of the absorbent composite and, though preferably no adhesive is utilized, the cover layer becomes slightly adhered to the MFC-coated SAP and carded fiber layer upon drying of the composite.

As FIG. 1A illustrates and as mentioned above, the absorbent composite comprises a nonwoven substrate that includes a nonwoven support sheet onto which carded fibers are applied. The carded fibers include MFC-coated SAP, which is suspended primarily in the upper portion of the carded fibers, thus forming the "absorbent" layer. Generally, the SAP has a basis weight in the absorbent layer from about 50-350 gsm (grams per square meter) and the MFC has a basis weight from about 5-20 gsm. Additionally, the carded fibers generally have a basis weight from about 18-100 gsm. The nonwoven support sheet preferably is polypropylene spunbond (PPSB) and has a basis weight from about 8-15 gsm.

In the preferred embodiment of the absorbent composite, the SAP basis weight is 350 gsm, the MFC basis weight is 14 gsm, the carded fiber basis weight is 80 gsm, and the nonwoven support sheet is 15 gsm PPSB. In addition, a tissue or 15 gsm nonwoven is added on top of the MFC-coated SAP layer.

Figure 3:
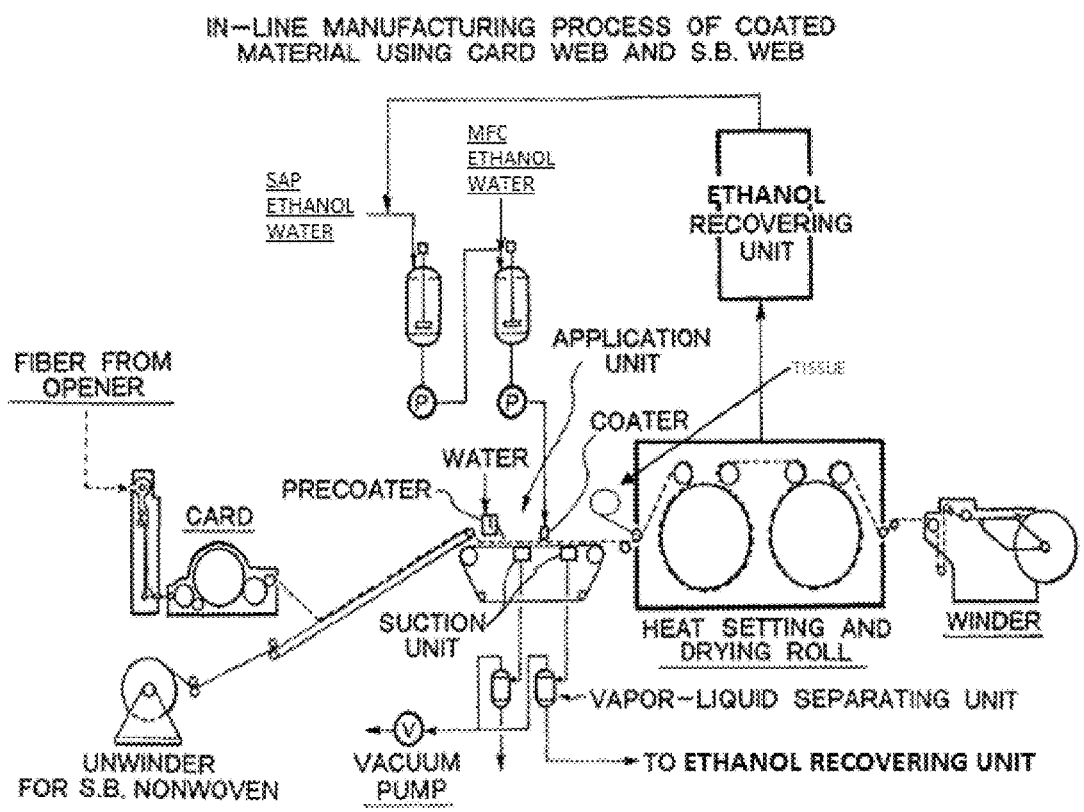
FIG. 3 is a schematic detailing the absorbent composite production process.

FIG. 3 schematically depicts the composite production process. The process begins with fibers, preferably polyester (PET) fibers, sent from an opener (not shown), which are fed into a carding machine. The carding operation separates and distributes (e.g., "combs") the fibers into a carded web. Binders, such as cellulosic and synthetic fibrous materials, bonding agents, soluble bonding mediums, such as cellulose acetate, and wet strength agents, are not used to form the carded web. The carded web exiting the carding process is laid on top of a nonwoven supporting sheet, typically made of PPSB, which is fed separately from the nonwoven material unwinder.

The resulting composite of carded web and support sheet is then fed to the application unit, which forms the nonwoven substrate by joining the carded web with the nonwoven support together through hydro-entanglement and applies the MFC-coated SAP slurry to the substrate. To do this, the application unit moves the composite of carded web and nonwoven support sheet along a planar treatment region, by means of an endless belt, to treat the composite of carded web and nonwoven support sheet firstly with waterjet entanglement, then a precoat solution, and finally a layer of slurry from a coater. The waterjet entanglement is applied generally in the form of a row of water jets to hydro-entangle the carded fibers and the nonwoven support sheet. The hydro-entanglement step can be thought of as a stitching process that stitches the loose carded fibers into the nonwoven support sheet. No binders are used in the hydro-entangling process as the binding is achieved through mechanical entanglement between the fibers and fibers. After the hydro-entangling process, the precoater wets the nonwoven substrate to prepare it for easier and more uniform application of the MFC-coated SAP slurry. This wetting solution can be water, solvent (ethanol) or a mixture of water and solvent. Thereafter, a coater applies a MFC-coated SAP slurry to the nonwoven substrate.

The MFC-coated SAP slurry is prepared by mixing, preferably homogenously, a SAP slurry with a MFC slurry. The SAP slurry is formed by adding, in the slurry preparation unit, SAP into a dispersing medium, preferably ethanol and water. The SAP may be selected from the many commercially available SAPs on the market today. For example, a preferred SAP is M331 offered by Nippon Shokubai. The SAP slurry is formed with only one type of SAP.

The MFC slurry is a mixture, preferably homogenous, of MFC in a solvent, preferably ethanol and water. In particular, MFC is prepared by the treatment and refinement of cellulose fibers obtained from wood pulp. The wood pulp fibers are first dispersed in water. This slurry of pulp fibers is then passed through a disc refiner. The disc refiner serves to beat and fibrillate the cellulose pulp fibers by the action of a single or dual rotating disc or blade. It is preferred that the slurry is passed through this disc refiner at least 10 times to create a fiber having an average length of about 5-10 microns. The MFC water suspension is then diluted with ethanol to form the MFC slurry.

Proper flow ratios of the SAP and MFC slurry streams are then fed into a static mixer to homogenously mix the components. The MFC particles assist in maintaining the SAP in solution in the slurry. This combined MFC-coated SAP slurry is then fed to the coater for the distribution of a uniform layer of MFC-coated SAP slurry onto the moving nonwoven substrate going through the treatment region. While the absorbent composite process does not use binders to bind the carded fibers to one another, the nonwoven support sheet fibers to one another, or the carded fibers to the nonwoven support sheet fibers, the MFC serves to bind the SAP particles to the carded fibers through hydrogen bonding.

Suction units, provided on the bottom surface of the endless belt in the treatment region, serve to remove any excess liquid from the carded web on the endless belt by means of a vacuum pump. Such removed liquids are recycled and recovered by means of a gas-liquid separation and condensation process in the gas-liquid separation unit.

After passing through the coater, a tissue or nonwoven cover layer is applied to the MFC-coated SAP surface of the nonwoven substrate and MFC-coated SAP slurry composite. The composite of nonwoven substrate, MFC-coated SAP, and cover layer is then fed through various heated drying rolls to remove any residual solvent and moisture. Further suction units and gas-separation units facilitate the collection and recovery of solvent. The composite then passes through a surfactant applicator (not shown), where an aqueous dispersion of surfactant is sprayed via a fine nozzle to disperse a fine mist of the surfactant solution over the entire area of the nonwoven substrate side of the composite. The surfactant is thus deposited uniformly onto the substrate to render the nonwoven substrate side of the composite hydrophilic. The formed absorbent composite is then wound onto a mother roll, which is sent to storage, or downstream to a slitter to divide the mother roll into narrower composite rolls and packing unit to be transferred into appropriate packages for use in a converting machine making absorbent products.

Figure 1B:
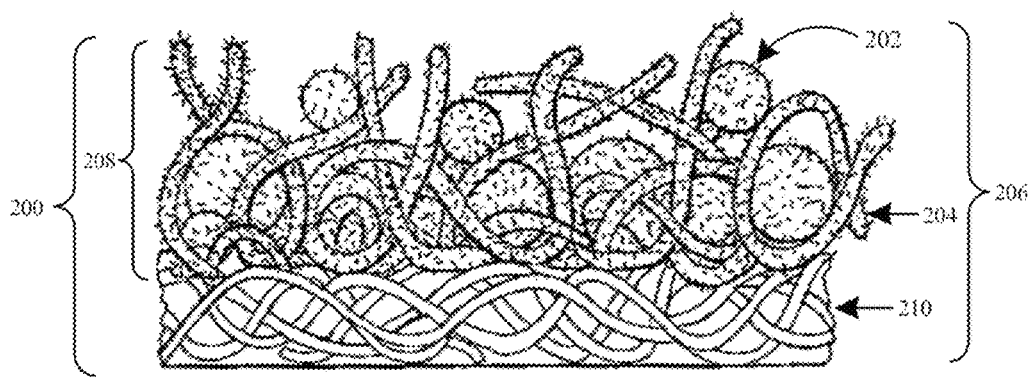
FIG. 1B depicts an alternative embodiment wherein the MFC-coated SAP 202 is disposed within the carded fiber web 204.

The absorbent composites manufacturing process produces the absorbent composites shown in FIGS. 1A and 1B. As shown in FIG. 1A, the concentration MFC-coated SAP is most concentrated at the top and decreases toward the nonwoven support sheet 210. The deposition of MFC-coated SAP particles in the manufacturing process can be controlled to achieve a concentration gradient that is gradual. The carded-fiber layer 208 and the nonwoven support sheet 210 may contain loose MFC that is not intermixed with SAP. As described, the MFC, whether loose or intermixed with SAP, does not act as a binder to bind either the carded fibers or nonwoven materials to themselves to form each respective layer. Also, the MFC does not act as a binder to bind the carded-fiber layer 208 and the nonwoven support sheet 210 to one another.

Post-Manufacturing Processing of the Absorbent Composite

It is a desirable feature of any absorbent article made from the absorbent composite that the product be soft and flexible. One of the potentially negative features of relatively high SAP loading is stiffness and hardness. Hardness and stiffness can lead to poor user perception of the resulting product and problems associated with poor fit. Hence, before the inclusion of the absorbent composite into an absorbent product, the absorbent composite may be subjected to post-production processing to achieve the desired softness. The methods by which this softening processing can be achieved are described below.

Figure 4A:
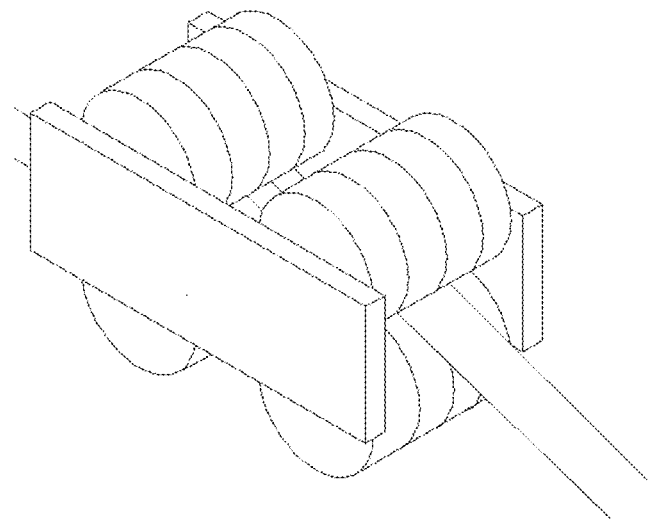
FIG. 4A depicts an optional post-manufacturing processing apparatus for the absorbent composite. A continuous length of composite is passed through geared rolls to soften the composite.
Figure 4B:
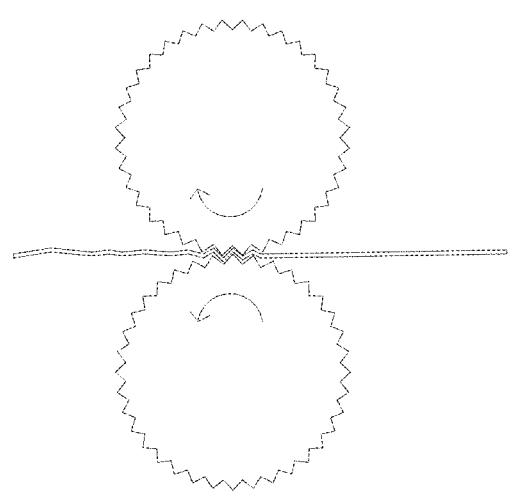
FIG. 4B is a side view of the composite passing through geared rolls. The composite bends around the gears, and the gap between the gears allows the composite to deform without breaking or fracturing the nonwoven web. The bending process promotes softness and flexibility of the composite.

The absorbent composite may be softened by running it through one or more pairs of interlocking geared rolls as shown in FIGS. 4A and 4B. The gap between the interlocking rolls is set so that the absorbent composite is deformed as it bends around the teeth of the interlocking gears. The deforming process softens the composite without breaking or fracturing the nonwoven web, maintaining the integrity of the composite. This deforming process also increases the flexibility of the composite and may promote a three-dimensional composite surface structure.

Figure 5A:
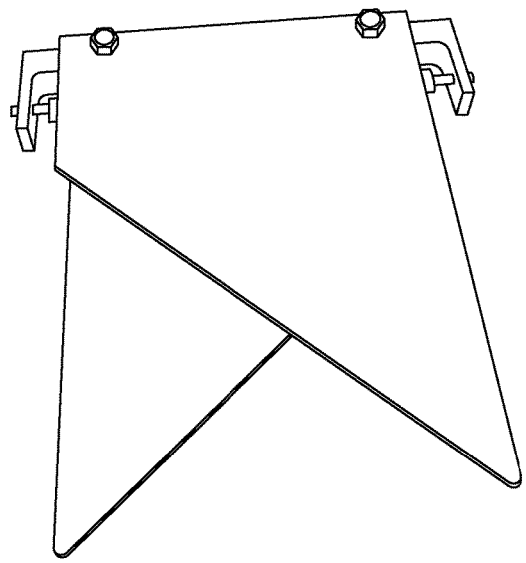
FIG. 5A illustrates a dual-edge softening apparatus for optional post-manufacturing softening of the absorbent composite.
Figure 5B:
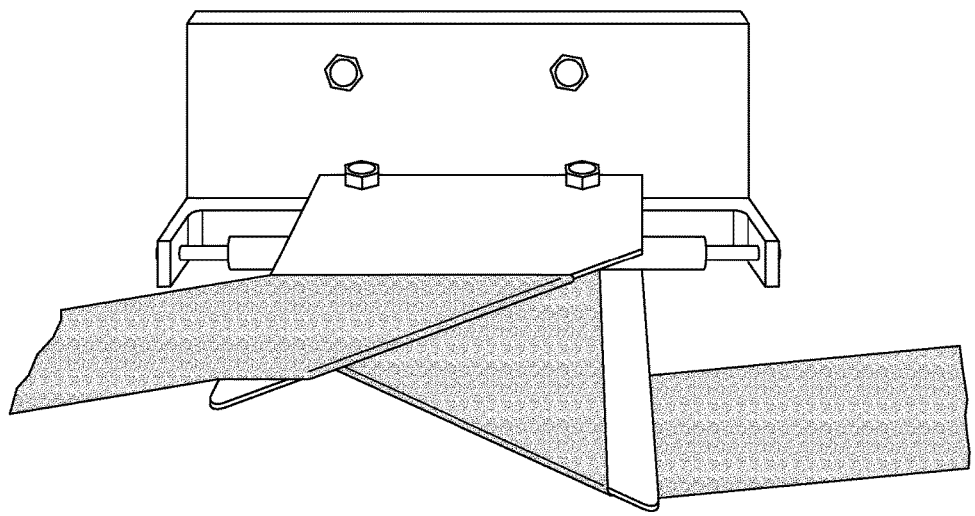
FIG. 5B depicts a continuous absorbent composite web passing through the dual-edge apparatus.

The absorbent composite may be softened by passing it through a dual-blade softening apparatus (FIG. 5A) that includes blades and a roller. FIG. 5B shows the apparatus in operation with the composite web threaded through the apparatus. The two angled edges of the apparatus transiently fold the moving composite web as it passes through the device. The transient folding fractures the continuous SAP layer and reduces composite stiffness. The composite web is kept under tension to keep the web on track and to enhance the softening effect. The constant movement of the composite web through the device ensures that the composite is not permanently folded. The continuous SAP layer is discomposed, but the structural integrity of the PPSB support sheet remains unaffected.

Figure 6A:
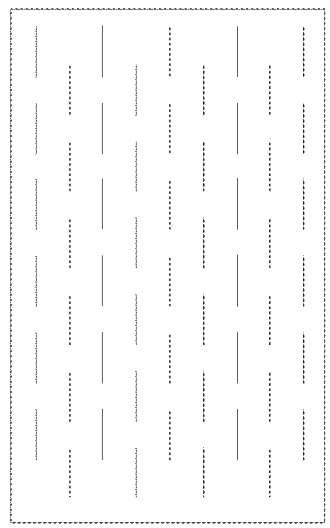
FIG. 6A illustrates further optional post-manufacturing processing of the absorbent composite. A plurality of slits have been imparted on the absorbent composite. The slits extend through all the layers of the composite which promote the flow of fluid through the composite and improve flexibility.

Further optional post-manufacturing processing of the absorbent composite involves introducing a plurality of discontinuous slits into the absorbent material, where the slits extend completely through all layers of the composite. The slitting process does not remove material, but instead results in short, capillary size passages in the composite. The slitted material benefits from improvements to the speed at which fluid can flow through and into the material and from improvements in flexibility. One such slit pattern is shown in FIG. 6A.

Figure 6B:
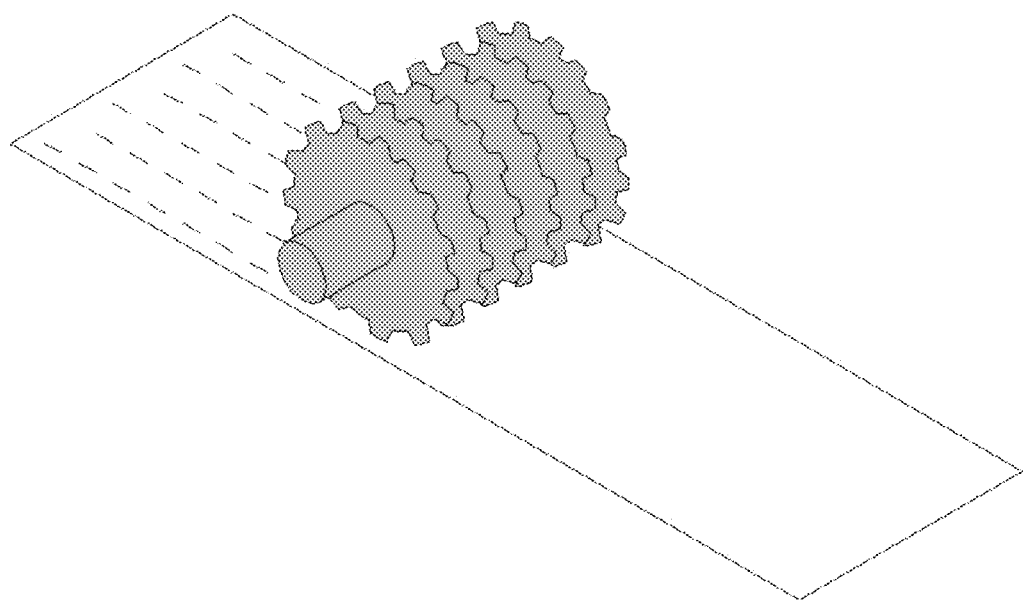
FIG. 6B illustrates the slitting process which involves a series of parallel cutting discs with notches or spaces along the disc edges. As the composite material is passed along the disc axis, the rotating discs and create a series of parallel slits in the absorbent composite. The discs may be altered to affect the number of slits per unit distance, the length of the slits, and the slitting pattern.

Various methods can be used to impart the plurality of slits to the absorbent material as described in further detail below. These methods do not involve a slitter, which is a cutting instrument used to divide an absorbent composite roll into narrower rolls for use. One preferred method of making slits involves the use of a series of cutting discs aligned in parallel over an anvil roll. The composite material is run between the cutting discs and the anvil roll. The cutting discs feature notches or spaces in the cutting blade, these spaces serving to create an incomplete cutting action so that a series of slits can be created during one revolution of the cutting disc. This process is illustrated in FIG. 6B.

The number, length and distribution of slits may vary depending on need and application. "Slit level" is a term used to describe the level of slits required and is defined as the ratio of total slit perimeter to unit planar area. As is apparent, slit level varies depending on the number of slits, slit length and slit distribution. For example, a core composite having a slit length of 12 mm, a separation between slits in the machine direction (the long dimension of the article) of 6 mm and a slit separation in the cross machine direction (the short dimension of the article) of 7.5 mm will have a slit level of 1.00 cm$^{-1}$.

$$\text{Slit level} = (1.2 \times 2)/(1.8 \times 0.75) = 1.00 \text{ cm}^{-1}$$

Absorbent Article

The absorbent composite can be used as an effective and efficient means of absorbing urine within an absorbent article, such as a diaper or training pants. The absorbent article production process begins with a roll of continuous absorbent composite. The composite is unrolled and sprayed with adhesive. Adhesive may be applied according to a number of methods known to those skilled in the art. For example, the adhesive may be sprayed, rolled, or spun onto the composite surface. The adhesive may be hydrophobic, hydrophilic, biodegradable, dio-derived, or combinations thereof. The preferred adhesive is hydrophilic. The concentration of adhesive varies between 1 and 100 gsm. Enough adhesive should be applied to cover at least 25% of the target area. The continuous composite web is wrapped with tissue or nonwoven in a C-fold configuration (FIG. 2). The tissue or nonwoven wrap overlaps to form a seam along the length of the composite. The composite web is then cut into individual, wrapped absorbent composites. The length of the individual composites may vary depending on the application.

Before being incorporated into an absorbent article, an acquisition distribution layer (ADL) may be placed above the absorbent composite such that the ADL is situated between the absorbent composite and the topsheet. The size and arrangement of the ADL may vary as desired. FIG. 7A. depicts an ADL, which is shorter and narrower than the composite on which it is situated. The ADL comprises synthetic fibers and does not contain latex binders. Upon a liquid insult, the liquid comes into contact with the ADL which distributes the liquid over an area larger than the initial area of insult and allows liquid to pass through to the composite. The distribution of the insult liquid over a larger area enhances the liquid uptake rate. The ADL is designed in such a way as to permit the flow of liquid in one direction, thereby preventing liquid from flowing back from the absorbent composite to the body.

Figure 7:
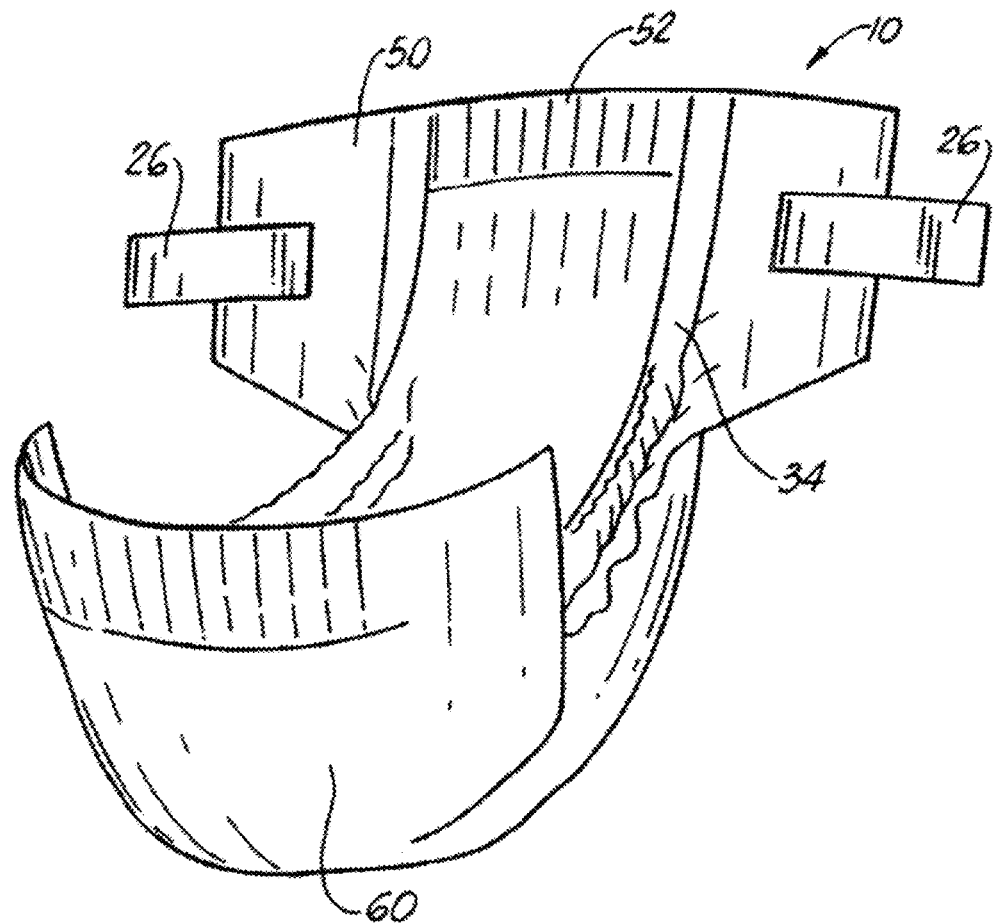
FIG. 7 is a three-dimensional view of an absorbent article of the present invention.
Figure 8:
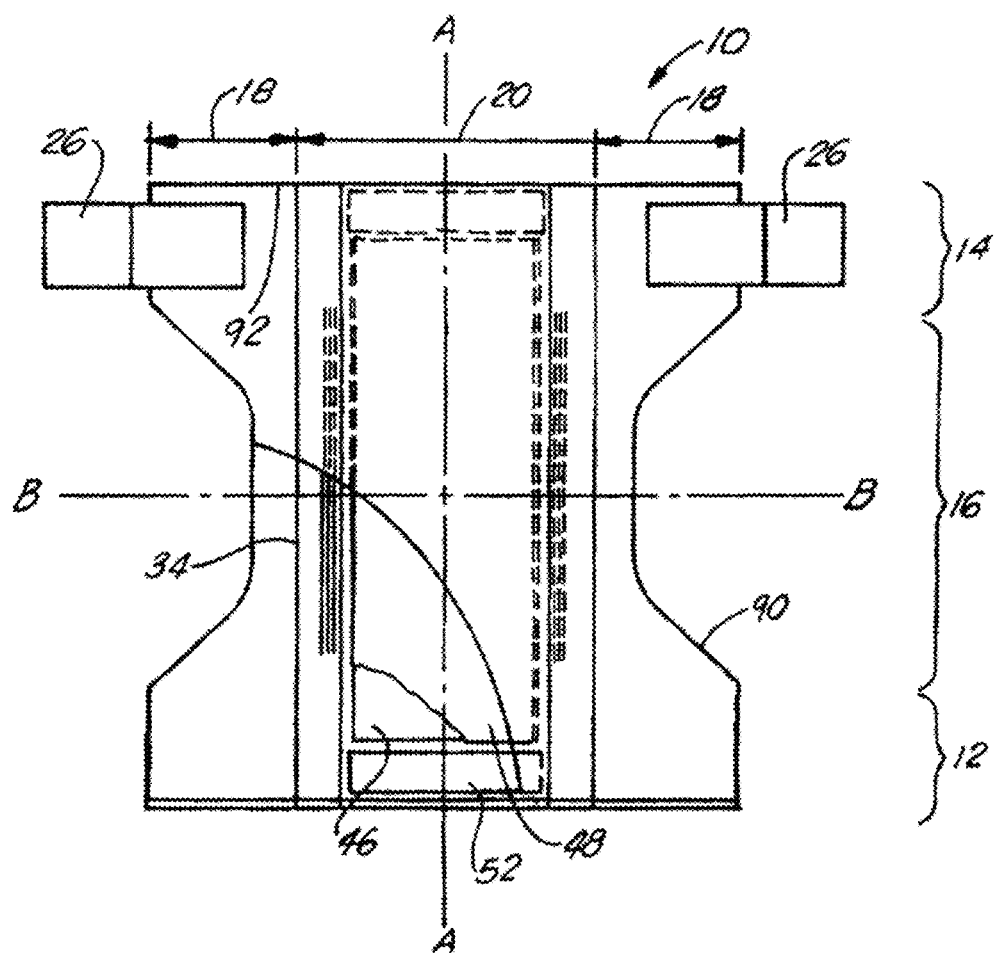
FIG. 8 is a top view of an absorbent article of the present invention.
Figure 9:
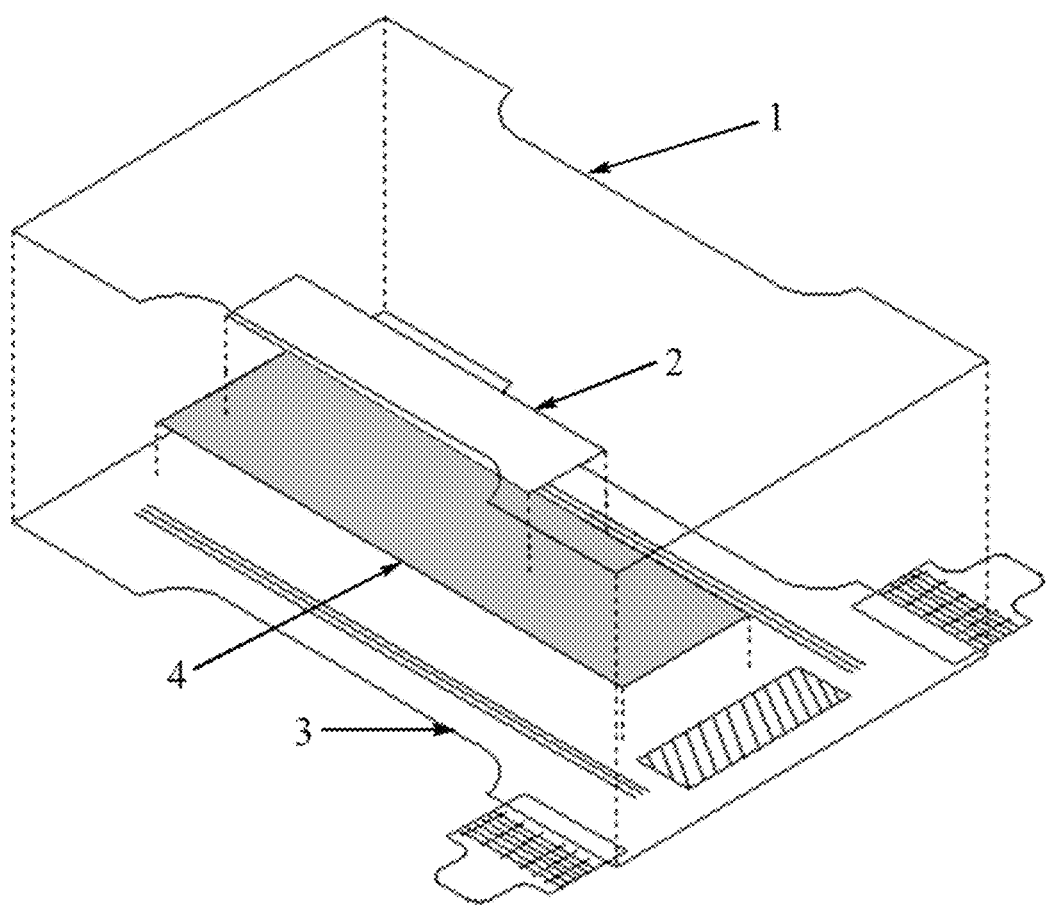
FIG. 9 is an expanded view of the absorbent article of the present invention.

The preferred embodiment of absorbent article includes a single absorbent composite with its nonwoven substrate facing the top sheet and the MFC-coated SAP layer facing the back sheet. FIGS. 7 and 8 illustrate the absorbent article in three-dimensional and flat configurations. FIG. 9 is an expanded view of the preferred absorbent article embodiment that includes a single absorbent composite. The diaper has a top sheet 1, an ADL 2 and a backsheet 3, all formed of materials well-known in the art. The diaper also includes an absorbent composite 4, which is disposed between the backsheet and topsheet. In the preferred embodiment, the core is inverted so that the nonwoven base layer is closer to the topsheet and the SAP layer faces away from the body.

Alternative Embodiments

In addition to the preferred embodiment of the absorbent composite described above, alternative embodiments may be manufactured wherein the component nature, relative amounts, and/or organization are varied. The basis weight of the SAP in the absorbent layer may range from about 50-650 gsm (grams per square meter) and the MFC basis weight may range from about 5-20 gsm. Additionally, the basis weight of the carded fibers may range from about 18-100 gsm. The nonwoven support sheet basis weight may range from about 8-15 gsm. The cover layer disposed above the MFC-coated SAP layer may comprise tissue or nonwoven and may further include a surfactant. In one embodiment, the carded fiber layer has a basis weight of 50 gsm. In one embodiment of the absorbent composite, the SAP layer has a basis weight of 250 gsm. In some embodiments, the disposition of the SAP layer may be altered; FIG. 1B illustrates an embodiment of the absorbent composite wherein the MFC-coated SAP lies substantially within the carded fiber web.

In an alternative embodiment, a small amount of short fibers are added to the SAP-MFC slurry to alter the characteristics of the resulting composite. In particular, the use of short-cut (¼" or less in length) staple fibers such as polyester, nylon, PET, can further improve the absorbent performance of the composite. Optionally, a short cut bicomponent binder fiber may added to the SAP-MFC sluffy promote composite integrity by causing the the low melting component of the binder fiber to melt during the drying process and form a stabilizing network within the SAP composite. The amount of short cut fibers added are between 0-10%.

The preferred embodiment for the absorbent article of the present invention includes a single absorbent composite, however some embodiments will utilize two absorbent composites. The two absorbent composites may vary in size and relative positioning within an absorbent article. The absorbent composite or composites can be readily incorporated into a wide variety of absorbent structures in an absorbent article. Multiple material layers of different lengths can be constructed to provide cores that have varying levels of absorbency along the length or width of the core. The cores can also be folded to provide useful structures for the intake and containment of fluids. Due to the nature of the manufacturing process, the absorbent composite has one face which is predominantly composed of SAP and MFC, and one face which is the nonwoven layer of the substrate. The absorbent composite or composites may be oriented with the SAP layer facing the body, or with the SAP layer facing away from the body.

Figure 10:
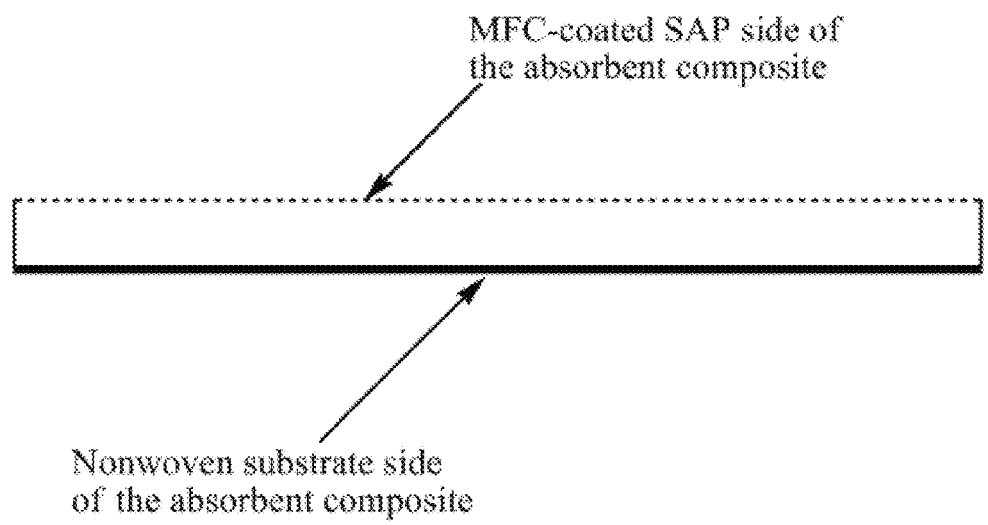
FIG. 10 is a simplified cross-section depicting the nonwoven substrate and the MFC-coated SAP side of the absorbent composite. The solid line represents the nonwoven substrate side of the composite and the horizontal dotted line represents the MFC-coated SAP side of the absorbent composite.

FIG. 10 illustrates the asymmetric structure of the absorbent composite. The bottom solid line represents the nonwoven substrate and the dotted line represents the MFC-coated SAP side of the absorbent composite. The composite may be oriented with either the nonwoven or the SAP side of the composite facing the body. Alternative composite configurations are illustrated in FIGS. 11 to 21, absorbent cores A-G.

Alternative Hybrid Absorbent Composite Production Processes

One embodiment of the present invention includes a hybrid absorbent composite production process wherein the SAP slurry preparation step is omitted and dry SAP is added uniformly to the web prior to the precoater (FIG. 18). The MFC slurry is still used and is added via the coater to the substrate now containing the SAP. The composite formed has essentially the same structure as the original composite process, but eliminates the SAP slurry unit operation and utilizes significantly less solvents in the composite manufacture.

The SAP is typically deposited using a particle scattering device (FIG. 19). In addition to uniform deposition, it can also be deposited non-uniformly, as in stripes in the machine direction or cross-machine direction. A patterned SAP distribution can also be achieved by using a patterned deposition SAP delivery roll wherein the pattern is defined by the distribution of concave areas or pockets in the rotating roll.

The hybrid manufacturing process for the absorbent composite comprises the following steps: (1) carding of fibers, for example, polyester (PET) to form a carded web; (2) placing the carded web on top of the nonwoven supporting sheet; (3) mechanically joining the carded web with the nonwoven supporting sheet through hydro-entanglement to form a nonwoven substrate; (4) applying dry SAP to the carded, nonwoven substrate; (5) preparing a MFC slurry by combining, preferably homogeneously, the MFC with a solvent, preferably a solution of ethanol and water (6) applying the MFC slurry to the SAP containing nonwoven substrate; (7) withdrawing excess liquid from the nonwoven substrate with a vacuum force; (7) placing a cover layer on top of the MFC-coated SAP surface; (8) drying the composite with heat and suction units to facilitate the collection and recovery of solvent; (9) optionally treating the nonwoven substrate side of the composite with surfactant; (10) optionally, winding the absorbent composite web into a mother roll; and (11) optionally, dividing the mother roll into narrower rolls of composite material using a slitter.

Absorbent Article Components

Backsheet

The diaper in FIGS. 7 and 8 employs a backsheet 60 that covers the core 46 and preferably extends beyond the core 46 toward the side edges 90 and end edges 92 of the diaper 10.

Topsheet

Similarly, the inventive absorbent composite may be utilized with or as the topsheet of an absorbent garment. The topsheet 50 is preferably soft, compliant, exhibits good strikethrough and a reduced tendency to rewet from a liquid previous material. The topsheet 50 is placed in close proximity to the skin of the wearer when the diaper 10 is worn. In this way, such a topsheet 50 permits bodily discharges to rapidly penetrate it so as to flow toward the core 46 more quickly, but not allowing such discharges to flow back through the topsheet 50. The topsheet 50 may be constructed from any one of a wide range of liquid and vapor permeable hydrophilic materials. The surface(s) of the topsheet may be treated with a surfactant so as to facilitate liquid transfer therethrough, especially at a central zone or area of the topsheet located over the core and an inner surface of the core. The topsheet may also be coated with a substance having rash preventing or rash reducing properties (e.g., aloe vera).

In one embodiment, the top sheet 50 is formed from an absorbent composite that covers substantially the entire area of the disposal absorbent article 10, including substantially all of the front waist region 12, back waist region 14, and crotch region 16. Further, the ear layer of the inner region 18 is formed from the same single topsheet material and, thus, may be referred to as being unitary with the topsheet 50 in forming lateral extensions of the topsheet material. Alternatively, the topsheet 50 may be formed from multiple different materials which vary across the width of the top sheet 50. Such a multiple piece design allows for creation of preferred properties and different zones of the topsheet.

Containment Walls

Now turning to FIGS. 7 and 8, in yet another aspect of the invention, the inventive disposable absorbent article 10 utilizes a pair of containment walls or cuffs 34 which employ the absorbent composite. Each containment wall 34 is a longitudinally extending wall structure preferably positioned on each side of the core 46 and spaced laterally from the longitudinal center. The longitudinal ends of the walls 34 may be attached, for example, to the topsheet 50 in the front and rear waist regions 12 and 14. Preferably, the ends of the containment wall 34 are tacked down inwardly and attached, for example, by adhesive to the web structure. Such a construction effectively biases the containment wall 34 inwardly and is generally considered to cause containment wall 34 to exhibit improved leakage prevention properties.

Preferably, the containment walls 34 are equipped with elastic members, which extend along a substantial length of the containment walls 34. In a common application, the elastic members are placed within the containment walls 34, preferably at the top of the containment walls 34 while in a stretched condition and then glued to the containment walls at least at their ends. When released or otherwise allowed relaxing, the elastic members retract inwardly. When the article 10 is worn, the elastic members function to contract the containment walls 34 about the buttocks and the thighs of the user in a manner, which effects a seal between the article 10, the buttocks and the thighs. The core 46 may be a single sheet of absorbent composite or multi-layered, as described above.

Optional Layers

The disposable absorbent article according to the invention may employ additional layers including an acquisition layer or surge layer 48, preferably situated between the topsheet and the core. One function of such an acquisition layer is to spread out or disperse liquid flow so that liquid is distributed more evenly over the core surface. This serves to slow down the flow so that the liquid has adequate time to be absorbed by the core. The acquisition layer also serves to prevent the core from being saturated locally, while a substantial remainder of the core is not absorbing any liquid.

Tape Tabs

The disposable absorbent article must be secured to the wearer. This is most important with respect to diapers since diapers are not pulled up by the wearer, like training pants or incontinent briefs, but are fastened around the wearer. Securing elements compliment the elastic members by effecting a quasi-seal between the wearer and the waistband and leg cuffs, so that liquid is contained within the article which is then absorbed; in other words, so that it does not leak through gaps between the wearer and the edge of the article. The securing elements may be adhesive, mechanical fasteners hook and loop features, or conceivably strings, i.e., anything that will secure one end of the article to the longitudinally opposite end. The securing elements may also be co-adhesive such that they adhere to each other but not other materials.

In the embodiment shown in the FIG. 7, the article 10 is affixed to the wearer by tape fasteners 26 which are permanently affixed to (e.g., sewn directly into) the backsheet 60. Alternatively, the article 10 may be training pants, pull-on diapers, and the like. In this configuration, the article 10 may or may not have tape fasteners 26.

Waistband

Waistbands employing elastic members 52 are positioned along the transverse portion of the article 10 so that when worn, the waistbands are positioned along the waist of the wearer. Generally, the waistband preferably creates a quasiseal against the waist (transverse elastic members 52) so that liquid waste does not leak from the regions between the waist elastic and the waist of the wearer. The quasi-seal is significant because, although the liquid may be eventually absorbed by filler material, the assault of liquid by the wearer may overwhelm the absorption rate capacity of the filler material. Hence, the waistbands contain the liquid while it is being absorbed. Secondly, the waistbands may have a capacity to absorb liquid (see, e.g., U.S. Pat. No. 5,601,544, which is hereby incorporated by reference).

The present invention is, therefore, well adapted to carry out the objects and attain the ends and the advantages mentioned, as well as others inherent therein. While presently preferred embodiments (in the form of a diaper) have been described, numerous changes to the details of construction, arrangement of the article's parts or components, and the steps to the processes may be made. For example, the various topsheets, backsheet, absorbent core, containment walls and other absorbent composite structures may be utilized in other parts of the article or with other articles other than diapers. Such changes will readily suggest themselves of those skilled in the art and are encompassed within the spirit of invention and in the scope of the appended claims.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A process for making an absorbent composite, comprising:
    applying super absorbent particles (SAP) to a nonwoven substrate, wherein the SAP is dry when applied to the nonwoven substrate;
    after applying the SAP to the nonwoven substrate, applying microfibrillated cellulose (MFC) to the nonwoven substrate to form WC-coated SAP; and
    placing a cover layer on top of the WC-coated SAP to form the absorbent composite wherein the cover layer comprises a tissue or a nonwoven fabric.

2. The process of claim 1, wherein applying the WC comprises applying a slurry including the WC and a solvent, and wherein the method further comprises, after placing the cover layer on top of the MFC-coated SAP to form the absorbent composite, drying the absorbent composite.

3. The process of claim 2, further comprising, after applying the SAP to the nonwoven substrate and prior to applying the slurry to the nonwoven substrate, applying a wetting solution to the nonwoven substrate.

4. The process of claim 3, wherein the wetting solution comprises water, ethanol, or a mixture of water and ethanol.

5. The process of claim 2, further comprising preparing the MFC slurry by combining the WC with the solvent.

6. The process of claim 5, wherein the solvent comprises water and ethanol.

7. The process of claim 2, further comprising, after applying the slurry and before placing the cover layer, withdrawing excess liquid from the nonwoven substrate.

8. The process of claim 7, wherein the excess liquid is withdrawn using a vacuum force.

9. The process of claim 2, wherein drying the absorbent composite comprises using heat and suction units to collect and recover the solvent of the slurry.

10. The process of claim 2, wherein, upon drying of the absorbent composite, the WC serves to bind the cover layer with the nonwoven substrate through hydrogen bonding.

11. The process of claim 2, wherein, upon drying of the absorbent composite, the WC serves to bind the SAP with the cover layer and with the nonwoven substrate through hydrogen bonding.

12. The process of claim 1, wherein the SAP is applied to the nonwoven substrate non-uniformly.

13. The process of claim 1, wherein the SAP is applied to the nonwoven substrate in a pattern.

14. The process of claim 1, wherein the SAP is applied to the nonwoven substrate using a particle scattering device.

15. The process of claim 1, further comprising:
carding of fibers to form a carded web;
placing the carded web on top of a nonwoven supporting sheet; and
mechanically joining the carded web with the nonwoven supporting sheet through hydro-entanglement to form the nonwoven substrate.

16. The process of claim 15, wherein the fibers are polyester fibers.

17. The process of claim 15, wherein carding the fibers comprises:
feeding the fibers into a carding machine; and
separating and distributing the fibers into the carded web, wherein binders, bonding agents, soluble bonding mediums, and wet strength agents are not used to form the carded web.

18. The process of claim 15, wherein the nonwoven supporting sheet comprises polypropylene spunbond.

19. The process of claim 1, further comprising treating a nonwoven substrate side of the absorbent composite with surfactant.

20. The process of claim 19, wherein the nonwoven substrate side of the absorbent composite is hydrophilic.

21. The process of claim 1, further comprises softening the absorbent composite.

22. An absorbent article comprising:
a multilayer absorbent core comprising:
a first absorbent composite, the first absorbent composite including a nonwoven substrate comprising a nonwoven support sheet hydro-entangled with a carded fiber web, a cover layer, and an absorbent layer positioned between the nonwoven substrate and the cover layer, the absorbent layer comprising super absorbent polymer particles coated with microfibrillated cellulose, wherein the first absorbent composite has an WC-coated SAP side and a nonwoven substrate side;
a second absorbent composite positioned adjacent the first absorbent composite, the second absorbent composite including a nonwoven substrate comprising a nonwoven support sheet hydro-entangled with a carded fiber web, a cover layer, and an absorbent layer positioned between the nonwoven substrate and the cover layer, the absorbent layer comprising super absorbent polymer particles coated with microfibrillated cellulose, wherein the second absorbent composite has an WC-coated SAP side and a nonwoven substrate side, wherein the nonwoven substrate side of the second absorbent composite is positioned adjacent the WC-coated SAP side of the first absorbent composite; and
an acquisition distribution layer positioned adjacent the multilayer absorbent.

23. The absorbent article of claim 22, wherein the acquisition distribution layer is positioned adjacent the WC-coated SAP side of the second absorbent composite or wherein the acquisition distribution layer is positioned adjacent the nonwoven substrate side of the first absorbent composite.

24. The absorbent article of claim 22, wherein the first and second absorbent composites vary in size and/or relative positioning within the absorbent article.

25. The absorbent article of claim 22, wherein the multilayer absorbent core is folded.

26. The absorbent article of claim 22, wherein the first absorbent composite is folded, and wherein the second absorbent composite is disposed above the folded, first absorbent composite.

27. The absorbent article of claim 22, wherein the first absorbent composite is wrapped around lateral edges of the second absorbent composite.

28. The absorbent article of claim 22, wherein the acquisition distribution layer is wrapped around lateral edges of the second absorbent composite.

29. The absorbent article of claim 22, further comprising:
a fluid-permeable topsheet; and
a fluid-impermeable backsheet;
wherein the multilayer absorbent core is disposed between the backsheet and the topsheet, and wherein the acquisition distribution layer is positioned between the multilayer absorbent core and the topsheet.

30. The absorbent article of claim 22, wherein the cover layer of the first absorbent composite comprises a tissue or a nonwoven fabric, and wherein the cover layer of the second absorbent composite comprises a tissue or a nonwoven fabric.

31. The absorbent article of claim 30, wherein, in each of the first and second absorbent composites, the microfibrillated cellulose binds the super absorbent polymer particles with the cover layer and with the nonwoven substrate through hydrogen bonding, and wherein the microfibrillated cellulose binds the cover layer with the nonwoven substrate through hydrogen bonding.

* * * * *